US009877482B2

(12) United States Patent
Wetcholowsky et al.

(10) Patent No.: US 9,877,482 B2
(45) Date of Patent: Jan. 30, 2018

(54) **USE OF SUCCINATE DEHYDROGENASE INHIBITORS FOR CONTROLLING *SCLEROTINIA* SSP**

(71) Applicant: BAYER INTELLECTUAL PROPERTY GMBH, Monheim (DE)

(72) Inventors: Ingo Wetcholowsky, Langenfeld (DE); Heiko Rieck, Burscheid (DE); Gilbert Labourdette, Paray le Monial (FR); Jose Augusto Geraldes, Ribeirao Preto (BR)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 14/978,645

(22) Filed: Dec. 22, 2015

(65) Prior Publication Data

US 2016/0205932 A1 Jul. 21, 2016

Related U.S. Application Data

(63) Continuation of application No. 12/792,430, filed on Jun. 2, 2010, now Pat. No. 9,232,794.

(30) Foreign Application Priority Data

Jun. 2, 2009 (EP) .................................... 09161671

(51) Int. Cl.
*A01N 43/40* (2006.01)
*A01N 37/24* (2006.01)
*A01N 43/56* (2006.01)

(52) U.S. Cl.
CPC ............ *A01N 43/40* (2013.01); *A01N 37/24* (2013.01); *A01N 43/56* (2013.01)

(58) Field of Classification Search
CPC ..................................................... A01N 43/40
See application file for complete search history.

(56) References Cited

U.S. PATENT DOCUMENTS

| | | | |
|---|---|---|---|
| 4,245,432 | A | 1/1981 | Dannelly |
| 4,272,417 | A | 6/1981 | Barke et al. |
| 4,761,373 | A | 8/1988 | Anderson et al. |
| 4,808,430 | A | 2/1989 | Kouno |
| 5,084,082 | A | 1/1992 | Sebastian |
| 5,141,870 | A | 8/1992 | Bedbrook et al. |
| 5,198,599 | A | 3/1993 | Thill |
| 5,273,894 | A | 12/1993 | Strauch et al. |
| 5,276,268 | A | 1/1994 | Strauch et al. |
| 5,304,732 | A | 4/1994 | Anderson et al. |
| 5,331,107 | A | 7/1994 | Anderson et al. |
| 5,378,824 | A | 1/1995 | Bedbrook et al. |
| 5,434,283 | A | 7/1995 | Wong et al. |
| 5,463,175 | A | 10/1995 | Barry et al. |
| 5,561,236 | A | 10/1996 | Leemans et al. |
| 5,605,011 | A | 2/1997 | Bedbrook et al. |
| 5,637,489 | A | 6/1997 | Strauch et al. |
| 5,646,024 | A | 7/1997 | Leemans et al. |
| 5,648,477 | A | 7/1997 | Leemans et al. |
| 5,712,107 | A | 1/1998 | Nichols |
| 5,731,180 | A | 3/1998 | Dietrich |
| 5,739,082 | A | 4/1998 | Donn |
| 5,767,361 | A | 6/1998 | Dietrich |
| 5,773,702 | A | 6/1998 | Penner et al. |
| 5,776,760 | A | 7/1998 | Barry et al. |
| 5,789,566 | A | 8/1998 | Bonhomme et al. |
| 5,824,790 | A | 10/1998 | Keeling et al. |
| 5,840,946 | A | 11/1998 | Wong et al. |
| 5,866,782 | A | 2/1999 | Iwabuchi et al. |
| 5,876,739 | A | 3/1999 | Turnblad et al. |
| 5,908,810 | A | 6/1999 | Donn |
| 5,908,975 | A | 6/1999 | Caimi et al. |
| 5,928,937 | A | 7/1999 | Kakefuda et al. |
| 5,965,755 | A | 10/1999 | Sernyk et al. |
| 5,969,169 | A | 10/1999 | Fan |
| 6,013,861 | A | 1/2000 | Bird et al. |
| 6,063,947 | A | 5/2000 | DeBonte et al. |
| 6,130,367 | A | 10/2000 | Kossmann et al. |
| 6,162,966 | A | 12/2000 | Kossmann et al. |
| 6,169,190 | B1 | 1/2001 | Lanuza et al. |
| 6,207,880 | B1 | 3/2001 | Kossmann et al. |
| 6,211,436 | B1 | 4/2001 | Kossmann et al. |
| 6,229,072 | B1 | 5/2001 | Burns et al. |
| 6,245,968 | B1 | 6/2001 | Boudec et al. |
| 6,255,561 | B1 | 7/2001 | Kossmann et al. |
| 6,255,563 | B1 | 7/2001 | Emmermann et al. |
| 6,268,549 | B1 | 7/2001 | Sailland et al. |
| 6,270,828 | B1 | 8/2001 | DeBonte et al. |
| 6,284,479 | B1 | 9/2001 | Nichols |
| 6,307,124 | B1 | 10/2001 | Kossmann et al. |
| 6,323,392 | B1 | 11/2001 | Charne |
| 6,566,585 | B1 | 5/2003 | Quanz |
| 6,590,141 | B1 | 7/2003 | Frohberg |
| 6,596,928 | B1 | 7/2003 | Landschütze |
| 6,734,341 | B2 | 5/2004 | Singletary et al. |
| 6,791,010 | B1 | 9/2004 | Frohberg |
| 6,812,010 | B1 | 11/2004 | Derose et al. |

(Continued)

FOREIGN PATENT DOCUMENTS

| | | | |
|---|---|---|---|
| EP | 1 389 614 | A1 | 2/2004 |
| EP | 2 071 953 | A1 | 12/2007 |

(Continued)

OTHER PUBLICATIONS

HGCA Topic Sheet No. 77, Home-Grown Cereals Authority, London, UK, pp. 1-2 (2004).*

(Continued)

*Primary Examiner* — John Pak
(74) *Attorney, Agent, or Firm* — McBee Moore Woodward & Vanik IP, LLC

(57) ABSTRACT

The invention relates to the use of succinate dehydrogenase inhibitors, especially of fluopyram, for controlling *Sclerotinia* ssp., to a method for treating plants or plant parts for controlling *Sclerotinia* ssp. and to a method for treating seed for controlling *Sclerotinia* ssp. in the seed and in the plants which grow from the seed, by treating the seed with a succinate dehydrogenase inhibitor.

7 Claims, No Drawings

(56) References Cited

U.S. PATENT DOCUMENTS

| | | | |
|---|---|---|---|
| 6,890,732 B1 | 5/2005 | Loerz et al. |
| 6,891,088 B1 | 5/2005 | Neuhaus et al. |
| 6,897,358 B2 | 5/2005 | Loerz et al. |
| 6,940,001 B1 | 9/2005 | Landschütze |
| 7,112,665 B1 | 9/2006 | Leemans et al. |
| 7,304,209 B2 | 12/2007 | Zink et al. |
| 7,547,819 B2 | 5/2009 | Elbe et al. |
| 9,232,794 B2 | 1/2016 | Wetcholowsky et al. |
| 2002/0031826 A1 | 3/2002 | Nichols |
| 2003/0176428 A1 | 9/2003 | Schneidersmann et al. |
| 2005/0257283 A1 | 11/2005 | Matringe et al. |
| 2008/0250533 A1 | 10/2008 | Frohberg |
| 2010/0324101 A1 | 12/2010 | Ebbinghaus et al. |

FOREIGN PATENT DOCUMENTS

| | | | |
|---|---|---|---|
| EP | 2039772 | * | 3/2009 |
| EP | 2 100 506 | A2 | 9/2009 |
| JP | 2008-133237 | | 6/2008 |
| WO | WO 89/10396 | A1 | 11/1989 |
| WO | WO 91/02069 | A1 | 2/1991 |
| WO | WO 94/04693 | A2 | 3/1994 |
| WO | WO 94/09144 | A1 | 4/1994 |
| WO | WO 94/11520 | A2 | 5/1994 |
| WO | WO 95/04826 | A1 | 2/1995 |
| WO | WO 95/26407 | A1 | 10/1995 |
| WO | WO 95/31553 | A1 | 11/1995 |
| WO | WO 95/35026 | A1 | 12/1995 |
| WO | WO 96/01904 | A1 | 1/1996 |
| WO | WO 96/19581 | A1 | 6/1996 |
| WO | WO 96/21023 | A1 | 7/1996 |
| WO | WO 96/33270 | A1 | 10/1996 |
| WO | WO 96/34968 | A2 | 11/1996 |
| WO | WO 97/20936 | A1 | 6/1997 |
| WO | WO 97/41218 | A1 | 11/1997 |
| WO | WO 97/45545 | A1 | 12/1997 |
| WO | WO 97/47806 | A1 | 12/1997 |
| WO | WO 97/47807 | A1 | 12/1997 |
| WO | WO 97/47808 | A1 | 12/1997 |
| WO | WO 98/00549 | A1 | 1/1998 |
| WO | WO 98/20145 | A2 | 5/1998 |
| WO | WO 98/22604 | A1 | 5/1998 |
| WO | WO 98/27212 | A1 | 6/1998 |
| WO | WO 98/27806 | A1 | 7/1998 |
| WO | WO 98/32326 | A2 | 7/1998 |
| WO | WO 98/39460 | A1 | 9/1998 |
| WO | WO 98/40503 | A1 | 9/1998 |
| WO | WO 99/12950 | A2 | 3/1999 |
| WO | WO 99/24593 | A1 | 5/1999 |
| WO | WO 99/53072 | A1 | 10/1999 |
| WO | WO 99/57965 | A1 | 11/1999 |
| WO | WO 99/66050 | A1 | 12/1999 |
| WO | WO 00/04173 | A1 | 1/2000 |
| WO | WO 00/11192 | A2 | 3/2000 |
| WO | WO 00/14249 | A1 | 3/2000 |
| WO | WO 00/28052 | A2 | 5/2000 |
| WO | WO 00/47727 | A2 | 8/2000 |
| WO | WO 00/66746 | A1 | 11/2000 |
| WO | WO 00/66747 | A1 | 11/2000 |
| WO | WO 00/73422 | A1 | 12/2000 |
| WO | WO 00/77229 | A2 | 12/2000 |
| WO | WO 01/14569 | A2 | 3/2001 |
| WO | WO 01/17333 | A1 | 3/2001 |
| WO | WO 01/19975 | A2 | 3/2001 |
| WO | WO 01/24615 | A1 | 4/2001 |
| WO | WO 01/65922 | A2 | 9/2001 |
| WO | WO 01/66704 | A2 | 9/2001 |
| WO | WO 01/98509 | A2 | 12/2001 |
| WO | WO 02/26995 | A1 | 4/2002 |
| WO | WO 02/28186 | A2 | 4/2002 |
| WO | WO 02/34923 | A2 | 5/2002 |
| WO | WO 02/36782 | A2 | 5/2002 |
| WO | WO 02/45485 | A1 | 6/2002 |
| WO | WO 02/079410 | A2 | 10/2002 |
| WO | WO 02/080675 | A1 | 10/2002 |
| WO | WO 02/101059 | A2 | 12/2002 |
| WO | WO 03/010149 | A1 | 2/2003 |
| WO | WO 03/013226 | A2 | 2/2003 |
| WO | WO 03/033540 | A2 | 4/2003 |
| WO | WO 03/071860 | A2 | 9/2003 |
| WO | WO 03/074491 | A1 | 9/2003 |
| WO | WO 03/092360 | A2 | 11/2003 |
| WO | WO 2004/016088 | A2 | 2/2004 |
| WO | WO 2004/035589 | A1 | 4/2004 |
| WO | WO 2004/040012 | A2 | 5/2004 |
| WO | WO 2004/053219 | A2 | 6/2004 |
| WO | WO 2004/056999 | A1 | 7/2004 |
| WO | WO 2004/078983 | A2 | 9/2004 |
| WO | WO 2004/090140 | A2 | 10/2004 |
| WO | WO 2004/106529 | A2 | 12/2004 |
| WO | WO 2005/002324 | A2 | 1/2005 |
| WO | WO 2005/002359 | A2 | 1/2005 |
| WO | WO 2005/012515 | A2 | 2/2005 |
| WO | WO 2005/017157 | A1 | 2/2005 |
| WO | WO 2005/020673 | A1 | 3/2005 |
| WO | WO 2005/030941 | A1 | 4/2005 |
| WO | WO 2005/030942 | A1 | 4/2005 |
| WO | WO 2005/077183 | A1 | 8/2005 |
| WO | WO 2005/093093 | A2 | 10/2005 |
| WO | WO 2005/095617 | A2 | 10/2005 |
| WO | WO 2005/095618 | A2 | 10/2005 |
| WO | WO 2005/095632 | A2 | 10/2005 |
| WO | WO 2005/123927 | A1 | 12/2005 |
| WO | WO 2006/015376 | A2 | 2/2006 |
| WO | WO 2006/015865 | A1 | 2/2006 |
| WO | WO 2006/015866 | A1 | 2/2006 |
| WO | WO 2006/018319 | A1 | 2/2006 |
| WO | WO 2006/021972 | A1 | 3/2006 |
| WO | WO 2006/024351 | A1 | 3/2006 |
| WO | WO 2006/032538 | A1 | 3/2006 |
| WO | WO 2006/060634 | A2 | 6/2006 |
| WO | WO 2006/063862 | A1 | 6/2006 |
| WO | WO 2006/072603 | A2 | 7/2006 |
| WO | WO 2006/103107 | A1 | 10/2006 |
| WO | WO 2006/108702 | A1 | 10/2006 |
| WO | WO 2006/131221 | A2 | 12/2006 |
| WO | WO 2006/133827 | A2 | 12/2006 |
| WO | WO 2006/136351 | A2 | 12/2006 |
| WO | WO 2007/009823 | A1 | 1/2007 |
| WO | WO 2007/017231 | A1 | 2/2007 |
| WO | WO 2007/024782 | A2 | 3/2007 |
| WO | WO 2007/027777 | A2 | 3/2007 |
| WO | WO 2007/039314 | A2 | 4/2007 |
| WO | WO 2007/039316 | A1 | 4/2007 |
| WO | WO 2007/118069 | A2 | 10/2007 |

OTHER PUBLICATIONS

Laemmlen, F., "Sclerotinia Diseases," University of California, Agriculture and Natural Resources, Publication 8042, pp. 1-5 (2001).*

English language Abstract of WIPO Patent Publication No. WO 99/57965 A1, European Patent Office, Espacenet database â World-wide (1999).

English language Abstract of WIPO Patent Publication No. WO 01/14569 A2, European Patent Office, Espacenet database â World-wide (2001).

English language Abstract of WIPO Patent Publication No. EP 1 389 614 A1, European Patent Office, Espacenet database â World-wide (2004).

English language Abstract of WIPO Patent Publication No. EP 2 071 953 A1, European Patent Office, Espacenet database â World-wide (2007).

English language Abstract of WIPO Patent Publication No. JP 2008-133237, European Patent Office, Espacenet database â World-wide (2008).

European Search Report for European Application No. EP 09 16 1671, European Patent Office, Netherlands, dated Jan. 7, 2010.

Kiryakov, I., "A method for screening the fungicide efficacy on Sclerotinia sclerotiorum (Lib.) de Bary," *Bulgarian Journal of Agricultural Science* 6(6):633-635, National Centre for Agrarian Sciences, Bulgaria, CABA Abstract No. 2001:114829 (2001).

(56) References Cited

OTHER PUBLICATIONS

Manandhar, J.B., et al., "Sclerotinia sclerotiorum in soybeans: pathogenic variability, host resistance, and seed infection," Proceedings of the 1998 International Sclerotinia Workshop, CABA Abstract No. 2000:14640 (2001).

* cited by examiner

USE OF SUCCINATE DEHYDROGENASE INHIBITORS FOR CONTROLLING *SCLEROTINIA* SSP

The invention relates to the use of succinate dehydrogenase inhibitors, especially of fluopyram, for controlling *Sclerotinia* ssp., to a method for treating plants or plant parts for controlling *Sclerotinia* ssp. and to a method for controlling *Sclerotinia* ssp. in seed and in plants which grow from the seed, by treating the seed with a succinate dehydrogenase inhibitor.

*Sclerotinia* ssp., especially *Sclerotinia sclerotiorum*, has sclerotia of size 5 to 20 mm and in some cases even larger. With the aid of the sclerotia, the fungi survive in the soil, on affected plant residues or on perennial weeds. If damp conditions persist for several weeks, *Sclerotinia sclerotiorum* can form the sexual stage: apothecia of 1 to a few cm in size and having ascospores grow from the sclerotia. For the germination of the sclerotia, temperatures must be between 6 and approx. 15° C. Shading of the sclerotia and damp soil are optimal for the germination. The ascospores are finally released and can cause infections on leaves and stems, provided that they hit weakened plant tissue or wounds. Fallen blossom which gets caught in leaf forks and side shoot branches promotes colonization of the spores and finally the germination thereof. The optimal temperature for the growth of the fungus is approx. 20° C., but it can still grow at 0° C. The sclerotia can survive for up to 10 years in the soil.

A conspicuous sign is yellowing plants, which also rapidly become prematurely ripe. In such plants, pale to brown discolorations are seen over the entire stem on the lower part of the main shoot. The inside of the stem under these discolorations is generally hollow, in which a white, cotton-like mycelium of the fungus proliferates. On this mycelium, small black grains, the sclerotia, are formed. At high air humidity or in the event of persistently wet weather, the mycelium and the sclerotia which appear thereon are also formed on the exterior of the stem.

*Sclerotinia sclerotiorum* is of great economic significance, in addition to oilseed rape, on the sunflower, on broad beans, soya, peas, alfalfa and a wide variety of different vegetable crops. Weeds are also affected.

*Sclerotinia sclerotiorum* occurs on almost all herbaceous crop plants in temperate climate zones and is one of the most feared harmful pathogens in soya cultivation.

There is therefore an urgent need for fungicides which enable sufficient control of *Sclerotinia* ssp. especially of *Sclerotinia sclerotiorum*, in crop plants, for example oilseed rape, sunflower, broad bean, soya, pea, alfalfa and a wide variety of different vegetable crops. *Sclerotinia sclerotiorum* is more preferably to be controlled in soya.

WO 03/010149 discloses the use of carboxamides of the formula I for controlling fungi, for example *Sclerotinia sclerotiorum* (page 31 line 1), on transgenic plants, for example soya, oilseed rape (pages 44-46). According to the invention, all plants, plant parts and/or propagation material are treated. Mixing partners disclosed for the abovementioned carboxamides are a series of fungicides on pages 36-42. However, it is not apparent from the teaching of the publication which specific carboxamides are suitable for treatment of *Sclerotinia* ssp.

WO 2006/015865 discloses mixtures comprising succinate dehydrogenase inhibitors, for example sedaxan and further active compounds (claims 1-10) against *Sclerotinia* spp. (page 59 line 7) for treatment of grass, soya, oilseed rape, sunflower, beans (page 58, line 4). Transgenic plants and the treatment thereof are disclosed on pages 51-52. However, it is not apparent from the teaching, of the publication which specific carboxamides are suitable for treatment of *Sclerotinia* ssp. More particularly, the suitability of sedaxan for treatment of *Sclerotinia* ssp. is not explicitly disclosed.

EP-A-1 389 614 discloses derivatives of the pyridinilethylbenzamide fungicides, for example fluopyram (claims 1-15), which are utilized against fungi of the *Sclerotinia sclerotiorum* genus (page 6 lines 38-39) on, for example, soya plants (page 6 line 4). However, it is not apparent from the teaching of the publication which specific pyridinilethylbenzamide fungicides are suitable for treatment of *Sclerotinia* ssp. More particularly, the suitability of fluopyram for treatment of *Sclerotinia* ssp. is not explicitly disclosed.

WO 2007/1017231 discloses the use of carboxamides of the formula I (claims 1-32) for seed treatment against fungi, for example *Sclerotinia sclerotiorum*, in plants, for example soya, oilseed rape and sunflower (page 16 lines 27-30). Mixing partners disclosed for the abovementioned carboxamides are a series of fungicides in claim 8. However, it is not apparent from the teaching of the publication which specific carboxamides of the formula I are suitable for treatment of *Sclerotinia* ssp.

WO 2006/131221 discloses the use of carboxamides of the formula I, for example the succinate dehydrogenase inhibitors boscalid and penthiopyrad (claim 4) for control of rust fungi, for example *Sclerotinia sclerotiorum*, on soya plants (page 28 line 29 to page 29 line 12). Transgenic plants which can be treated, for example soya plants, are likewise disclosed (para. 2, page 37, claim 6). Seed treatment is disclosed in para. 2, page 36. Mixing partners disclosed for the abovementioned carboxamides are a series of fungicides on pages 31-32. However, it is not apparent from the teaching of the publication which specific carboxamides of the formula I are suitable for treatment of *Sclerotinia* ssp. More particularly, the suitability of boscalid or penthiopyrad for treatment of *Sclerotinia* ssp. is not disclosed explicitly.

WO 2007/118069 discloses a method for treating grass or grass seed against fungi, for example *Sclerotinia* ssp. (Claims 11-15) by means of active carboxamides of the formula I (e.g. isopyrazam). Mixing partners disclosed for the abovementioned carboxamides are a series of fungicides on pages 19-20. However, it is not apparent from this publication either which specific carboxamides of the formula I are suitable for treatment of *Sclerotinia* ssp.

JP 2008/133237 discloses a method for soil treatment in the case of plants, for example beans, against fungi of the *Sclerotinia sclerotiorum* species [0007] by means of pyrazolecarboxamides, for example penthiopyrad [0001].

It has now been found that, surprisingly, succinate dehydrogenase inhibitors selected from the group consisting of fluopyram, isopyrazam, boscalid. N-[2-(1,3-dimethylbutyl)phenyl]-5-fluoro-1,3-dimethyl-1H-pyrazole-4-carboxamide, sedaxan, N-(3',4'-dichlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-N-[2-(1,1,2,3,3,3-hexafluoropropoxy)phenyl]-1-methyl-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-1-methyl-N-(3',4',5'-trifluorobiphenyl-2-yl)-1H-pyrazole-4-carboxamide, N-[2-(2,4-dichlorophenyl)-2-methoxy-1-methylethyl]-3-difluoromethyl-1-methyl-1H-pyrazole-4-carboxamide, flutolanil and bixafen, especially fluopyram, are outstandingly suitable for control of *Sclerotinia* ssp, especially of *Sclerotinia sclerotiorum*, in crop plants, for example oilseed rape, sunflower, broad bean, soya, pea, alfalfa and vegetable crops, especially in soya.

However, the aforementioned plants merely constitute examples. In principle, it is possible to treat any plant affected by *Sclerotinia* ssp. with the succinate dehydrogenase inhibitors.

The use of fluopyram for control of *Sclerotinia sclerotiorum* in soya has been found to be particularly advantageous.

In an alternative embodiment of the invention, combinations comprising prothioconazole and a further fungicide selected from the group consisting of azoxystrobin, picoxystrobin, pyraclostrobin, iprodione, fludioxonyl, propiconazole, epoxiconazole, cyproconazole, tebuconazole, procimidone (Sialex from Sumitomo), fluazinam, carbendazim, metaminostrobin can be used for control of *Sclerotinia sclerotiorum* in soya.

The combination of prothioconazole and trifloxystrobin is more preferably suitable for control of *Sclerotinia sclerotiorum* in soya.

The present invention accordingly provides for the use of succinate dehydrogenase inhibitors, especially of fluopyram, for control of *Sclerotinia sclerotiorum.*

In the context of the present invention, succinate dehydrogenasc inhibitors are all active ingredients which possess an inhibiting effect on the enzyme, succinate dehydrogenase, in the mitochondrial respiratory chain. In a preferred embodiment of the present invention, the succinate dehydrogenase inhibitors are selected from the group consisting of fluopyram, isopyrazam, boscalid, penthiopyrad, N-[2-(1, 3-dimethylbutyl)phenyl]-5-fluoro-1,3-dimethyl-1H-pyrazole-4-carboxamide, sedaxan, N-(3',4'-dichlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-N-[2-(1,1,2,3,3,3-hexafluoropropoxy) phenyl]-1-methyl-1H-pyrazole-4-carboxamide, 3-trifluoromethyl)-1-methyl-N-[2-(1,1,2,2-(tetrafluoroethoxy)phenyl]-1H-pyrazole-4-carboxamide, 3-(difluoromethyl)-1-methyl-N-(3',4',5'-trifluorobiphenyl-2-yl)-1H-pyrazole-4-carboxamide, N-[2-(2,4-dichlorophenyl)-2-methoxy-1-methylethyl]-3-difluoromethyl-1-methyl-1H-pyrazole-4-carboxamide, flutolanil and bixafen, and from mixtures of these compounds. In a particularly preferred embodiment of the present invention, the succinate dehydrogenase inhibitor is fluopyram.

Fluopyram, which has the chemical name N-{[3-chloro-5-(trifluoromethyl)-2-pyridinyl]ethyl}-2,6-dichlorobenzamide, and suitable processes for preparation thereof, proceeding from commercially available starting materials, are described in EP-A-1 389 614.

Bixafen, which has the chemical name N-(3',4'-dichloro-5-fluoro-1,1'-biphenyl-2-yl)-3-(difluoromethyl)-1-methyl-1H-pyrazole-4-carboxamide, and suitable processes for preparation thereof, proceeding from commercially available starting materials, are described in WO 03/070705.

N-[2-(1,3-Dimethylbutyl)phenyl]-5-fluoro-1,3-dimethyl-1H-pyrazole-4-carbaxamide (penflufen) and suitable processes for preparation thereof, proceeding from commercially available starting materials, are described in WO 03/010149.

Sedaxan is a mixture comprising the two cis isomers of 2'-[(1RS,2RS)-1,1'-bicycloprop-2-yl]-3-(difluoromethyl)-1-methylpyrazole-4-carboxamide and the two trans isomers of 2'-[(1RS,2SR)-1,1'-bicycloprop-2-yl]-3-(difluoromethyl)-1-methylpyrazole-4-carboxamide. Sedaxan and suitable processes for preparation thereof, proceeding from commercially available stalling materials, are described in WO 03/074491, WO 2006/015865 and WO 2006/015866.

Isopyrazam is a mixture comprising the two syn isomers of 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and the two anti isomers of 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide. Isopyrazam and suitable processes for preparation thereof, proceeding from commercially available starting materials, are described in WO 2004/035589.

Penthiopyrad, which has the chemical name (RS)—N-[2-(1,3-dimethylbutyl)-3-thienyl]-1-methyl-3-(trifluoromethyl)pyrazole-4-carboxamide, and suitable processes for preparation thereof, proceeding from commercially available starting materials, are described in EP-A-0 737 682.

Boscalid, which has the chemical name 2-chloro-N-(4'-chlorobiphenyl-2-yl)nicotinamide, and suitable processes for preparation thereof, proceeding from commercially available starting materials, are described in DE-A 195 31 813.

N-[2-(2,4-Dichlorophenyl)-2-methoxy-1-methylethyl]-3-difluoromethyl-1-methyl-1H-pyrazole-4-carboxamide is present as a mixture of 4 stereoisomers. Suitable processes for preparation thereof, proceeding from commercially available starting materials, are described in WO 2008/148570. The stereoisomers N-[(1R,2S)-2-(2,4-dichlorophenyl)-2-methoxy-1-methylethyl]-(+)-3-difluoromethyl-1-methyl-1H-pyrazole-4-carboxamide, N-[(1S,2R)-2-(2,4-dichlorophenyl)-2-methoxy-1-methylethyl]-(+)-3-difluoromethyl-1-methyl-1H-pyrazole-4-carboxamide; N-[(1R,2R)-2-(2,4-dichlorophenyl)-2-methoxy-1-methylethyl]-(−)-3-difluoromethyl-1-methyl-1H-pyrazole-4-carboxamide and N-[(1S,2S)-2-(2,4-dichlorophenyl)-2-methoxy-1-methylethyl]-(+)-3-difluoromethyl-1-methyl-1H-pyrazole-4-carboxamide can be separated from one another by HPLC using a chiral stationary phase, as described, for example, in WO 2010/000612.

N-(3',4'-Dichlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-N-[2-(1,1,2,3,3,3-hexafluoropropoxy)phenyl]-1-methyl-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-1-methyl-N-(3',4',5'-trifluorobiphenyl-2-yl)-1H-pyrazole-4-carboxamide (fluxapyroxad) and suitable processes for preparation thereof, proceeding from commercially available starting materials, are described in WO 2005/123690.

In the context of the present invention, "control of *Sclerotinia* ssp." means a significant reduction in infestation by *Sclerotinia* ssp., compared with the untreated plant, preferably a significant reduction (by 40-79%), compared with the untreated plant (100%), more preferably, the infection by *Sclerotinia* ssp. is entirely suppressed (by 70-100%). The control may be curative, i.e. for treatment of already infected plants, or protective, for protection of plants which have not yet been infected.

More particularly, the inventive use exhibits the advantages described on plants and plant parts or seed in spray application, in seed treatment, in drip and drench applications, chemigation, i.e. by addition of the active ingredients to the irrigation water, and in hydroponic/mineral systems.

Combinations of the appropriate succinate dehydrogenase inhibitors, preferably of fluopyram, with substances including insecticides, fungicides and bactericides, fertilizers, growth regulators, can likewise find use in the control of plant diseases in the context of the present invention. The combined use of appropriate succinate dehydrogenase inhibitors, preferably of fluopyram, with genetically modified cultivars, especially of transgenic soya cultivars, is additionally likewise possible.

In the context of the present invention, a plant is preferably understood to mean a plant at or after the stage of leaf development (at or after BBCH stage 10 according to the BBCH monograph from the German Federal Biological Research Centre for Agriculture and Forestry, 2nd edition, 2001). In the context of the present invention, the term "plant" is also understood to mean seed or seedlings.

In one embodiment, it is possible, for example, that the succinate dehydrogenase inhibitors envisaged in accordance with the invention, preferably fluopyram, are applied by spray application to appropriate plants or plant parts to be treated.

The use of the succinate dehydrogenase inhibitors envisaged in accordance with the invention, preferably of fluopyram, is effected preferably with a dosage between 0.01 and 3 kg/ha, more preferably between 0.05 and 2 kg/ha, especially preferably between 0.1 and 1 kg/ha.

Depending on their particular physical and/or chemical properties, the succinate dehydrogenase inhibitors, preferably fluopyram, can be converted in accordance with the invention to the customary formulations, such as solutions, emulsions, suspensions, powders, foams, pastes, granules, aerosols and microencapsulations in polymeric substances and in coating materials for seed, and also ULV cool and warm fogging formulations.

These formulations are produced in a known manner, for example by mixing the active ingredients with extenders, i.e. liquid solvents, liquefied gases under pressure and/or solid carriers, optionally using surfactants, i.e. emulsifiers and/or dispersants, and/or foam formers. If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are understood to mean those liquids which are gaseous at standard temperature and under standard pressure, for example aerosol propellants such as halohydrocarbons, or else butane, propane, nitrogen and carbon dioxide. Useful solid carriers are: for example natural rock flours such as kaolins, clays, talc, chalk, quartz, attapulgite, montmorillonite or diatomaceous earth, and synthetic rock flours such as finely divided silica, alumina and silicates. Useful solid carriers for granules are: for example crushed and fractionated natural rocks such as calcite, pumice, marble, sepiolite, dolomite, and synthetic granules of inorganic and organic flours, and also granules of organic material such as sawdust, coconut shells, maize cobs and tobacco stalks. Useful emulsifiers and/or foam generators are: for example nonionic and anionic emulsifiers, such as polyoxyethylene fatty acid esters, polyoxyethylene fatty alcohol ethers, for example alkylaryl polyglycol ethers, alkylsulphonates alkyl sulphates, arylsulphonates, or else protein hydrolysates. Useful dispersants include: for example lignosulphite waste liquors and methylcellulose.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

It is possible to use colorants such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

The formulations contain generally between 0.1 and 95 percent by weight of active ingredient, preferably between 0.5 and 90%.

Seed Treatment

The treatment of the seed of plants has been known for a long time and is the subject of constant improvements. Nevertheless, the treatment of seed gives rise to a series of problems which cannot always be solved in a satisfactory manner. For instance, it is desirable to develop methods for protecting the seed, the germinating plant and the resulting plants or plant parts, which dispense with, or at least significantly reduce, the additional deployment of crop protection products after planting or after emergence of the plants. It is additionally desirable to optimize the amount of active ingredient used in such a way as to provide the best possible protection for the seed and the germinating plant from attack by *Sclerotinia* ssp., but without damaging the plant itself by the active ingredient used.

The present invention therefore relates more particularly also to a method for treating seed to control *Sclerotinia* ssp. in the plants which grow from the seed, by treating the seed with a succinate dehydrogenase inhibitor. The seed is more preferably soya seed, for example.

The invention likewise relates to the use of succinate dehydrogenase inhibitors for treatment of seed to control *Sclerotinia* ssp in the seed, the germinating plant and the plants or plant parts which grow therefrom.

One of the advantages of the present invention is that, owing to the particular systemic properties of the succinate dehydrogenase inhibitors, preferably of fluopyram, the treatment of the seed with succinate dehydrogenase inhibitors, preferably with fluopyram, enables not only the control of *Sclerotinia* ssp. on the seed itself, but also on the plants which originate therefrom after emergence. In this way, the immediate treatment of the crop at the time of sowing or shortly thereafter can be dispensed with.

It is likewise considered to be advantageous that the succinate dehydrogenase inhibitors, preferably fluopyram, can especially also be used in transgenic seed.

The succinate dehydrogenase inhibitors, preferably fluopyram, are suitable for protection of seed of any plant cultivar which is used in agriculture, in greenhouses, in forests or in horticulture. More particularly, the seed is that of cereals (such as wheat, barley, rye, millet and oats), maize, cotton, soya, rice, potatoes, sunflower, bean, coffee, beet (e.g. sugar beet and fodder beet), peanut, vegetables (such as tomato, cucumber, onions and lettuce), lawns and ornamental plants. Of particular significance is the treatment of the seed of cereals (such as wheat, barley, rye and oats), maize and rice.

In the context of the present invention, the succinate dehydrogenase inhibitor, preferably fluopyram, is applied to the seed alone or in a suitable formulation. Preferably, the seed is treated in a state in which it is stable enough to avoid damage during treatment. In general, the seed may be treated at any time between harvest and sowing. The seed typically used has been separated from the plant and freed from cobs, shells, stalks, coats, hairs or the fruit flesh. For example, it is possible to use seed which has been harvested, cleaned and dried to a moisture content of less than 15% by weight. Alternatively, it is also possible to use seed which, after drying, for example, has been treated with water and then dried again.

When treating the seed, it must generally be ensured that the amount of the succinate dehydrogenase inhibitors, preferably of the bixafen, applied to the seed and/or of further additives is selected such that the germination of the seed is not impaired, and that the resulting plant is not damaged. This should be noted in particular in the case of active ingredients which can have phytotoxic effects at particular application rates.

The succinate dehydrogenase inhibitors, preferably fluopyram, can be applied directly, i.e. without containing any further components and without having been diluted. In general, it is preferable to apply the succinate dehydrogenase inhibitors, preferably fluopyram, to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The succinate dehydrogenase inhibitors usable in accordance with the invention, preferably fluopyram, can be converted to the customary seed dressing formulations, such as solutions, emulsions, suspensions, powders, foams, slurries or other coating materials for seed, and also ULV formulations.

These formulations are produced in a known manner, by mixing the active ingredients or active ingredient combinations with customary additives, for example customary extenders and solvents or diluents, dyes, wetting agents, dispersants, emulsifiers, defoamers, preservatives, secondary thickeners, stickers, gibberellins and also water.

Useful dyes which may be present in the seed dressing formulations usable in accordance with the invention are all dyes customary for such purposes. It is possible to use both sparingly water-soluble pigments and water-soluble dyes. Examples include the dyes known under the Rhodamine B, C.I. Pigment Red 112 and C.I. Solvent Red 1 names.

The wetting agents which may be present in the seed dressing formulations usable in accordance with the invention include all substances which promote wetting and are customary for formulation of active agrochemical ingredients. Usable with preference are alkyl naphthalenesulphonates, such as diisopropyl or diisobutyl naphthalenesulphonate.

The dispersants and/or emulsifiers which may be present in the seed dressing formulations usable in accordance with the invention include all nonionic, anionic and cationic disperants which are customary for formulation of active agrochemical ingredients. Usable with preference are nonionic or anionic dispersants or mixtures of nonionic or anionic dispersants. Suitable nonionic dispersants include especially ethylene oxide-propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

The defoamers which may be present in the seed dressing formulations usable in accordance with the invention include all foam-inhibiting substances customary for formulation of active agrochemical ingredients. Usable with preference are silicone defoamers and magnesium stearate.

The preservatives which may be present in the seed dressing formulations usable in accordance with the invention include all substances usable for such purposes in agrochemical formulations. Examples include dichlorophene and benzyl alcohol hemiformal.

Useful secondary thickeners which may be present in the seed dressing formulations usable in accordance with the invention include all substances usable for such purposes in agrochemical formulations. Preferred examples include cellulose derivatives, acrylic acid derivatives, xanthan, modified clays and finely divided silica.

Useful stickers which may be present in the seed dressing formulations usable in accordance with the invention are all customary binders usable in seed dressing compositions. Preferred examples include polyvinylpyrrolidone, polyvinyl acetate, polyvinyl alcohol and tylose.

The gibberellins which may be present in the seed dressing formulations usable in accordance with the invention are preferably gibberellins A1 A3 (=gibberellic acid). A4 and A7, particular preference being given to using gibberellic acid. The gibberellins are known (cf. R. Wegler "Chemie der Pflanzenschutz-und Schädlingsbekämpfungsmittel" [Chemistry of Crop Protection and Pest Control Compositions], vol. 2, Springer Verlag, 1970, p. 401-412).

The seed dressing formulations usable in accordance with the invention can be used to treat a wide variety of different kinds of seed either directly or after preceding dilution with water. For instance, the concentrates or the preparations obtainable therefrom by dilution with water can be used to dress the seed of cereals, such as wheat, barley, rye, oats and triticale, and the seed of maize, rice, oilseed rape, peas, beans, cotton, sunflowers and beet, or else vegetable seeds of a wide variety of different kinds. The seed dressing preparations usable in accordance with the invention or the dilute preparations thereof can also be used to dress seed of transgenic plants. In this case, it is also possible for additional synergistic effects to occur in interaction with substances formed by expression.

For treatment of seed with the seed dressing formulations usable in accordance with the invention, or the preparations prepared therefrom by adding water, all mixing units usable customarily for the seed dressing are useful. Specifically, the seed dressing procedure is to introduce the seed into a mixer, to add the particular desired amount of seed dressing, formulations, either as such or after preceding dilution with water, and to mix until the formulation is distributed homogeneously on the seed. This may be followed by a drying operation.

The application rate of seed dressing formulations usable in accordance with the invention may vary within a relatively wide range. It is guided by the particular content of the active ingredients in the formulations and by the seed. The application rates of active ingredient combinations are generally between 0.001 and 50 g per kilogram of seed, preferably between 0.01 and 15 g per kilogram of seed.

Particular preference is given in accordance with the invention to treating plants of the plant cultivars which are each commercially available or in use. Plant cultivars are understood to mean plants which have new properties ("traits") and which have been obtained by conventional breeding, by mutagenesis or with the aid of recombinant DNA techniques. Crop plants may accordingly be plants which can be obtained by conventional breeding and optimization methods or by biotechnology and genetic engineering methods or combinations of these methods, including the transgenic plants and including the plant varieties which can and cannot be protected by plant variety rights.

The method according to the invention can thus also be used for the treatment of genetically modified organisms (GMOs), for example plants or seeds. Genetically modified plants (or transgenic plants) are plants in which a heterologous gene has been integrated stably into the genome. The term "heterologous gene" means essentially a gene which is provided or assembled outside the plant and which, on introduction into the cell nucleus genome, imparts new or improved agronomic or other properties to the chloroplast genome or the mitochondrial genome of the transformed plant by virtue of it expressing a protein or polypeptide of interest or by virtue of another gene which is present in the plant, or other genes which are present in the plant, being downregulated or silenced (for example by means of antisense technology, co-suppression technology or RNAi technology [RNA interference]). A heterologous gene present in the genome is likewise referred to as a transgene. A transgene which is defined by its specific presence in the plant genome is referred to as a transformation or transgenic event.

Plants and plant cultivars which are preferably treated according to the invention include all plants which have genetic material which imparts particularly advantageous, useful traits to these plants (whether obtained by breeding and/or biotechnological means).

Plants and plant cultivars which may also be treated in according to invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients or shade avoidance.

Plants and plant cultivars which may also be treated according to the invention are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may also be treated according to the invention are hybrid plants that already express the characteristic of heterosis or hybrid vigour which generally results in higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in maize) be produced by detasseling, i.e. the mechanical removal of the male reproductive organs (or male flowers), but, more typically, male sterility is the result of genetic determinants in the plant genome. In that case, and especially when seed is the desired product to be harvested from the hybrid plants, it is typically useful to ensure that male fertility in hybrid plants that contain the genetic determinants responsible for the male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmatic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may likewise be treated according to the invention are herbicide-tolerant plants, i.e. plants made tolerant to one or more given herbicides. Such plants can be obtained either b) genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an Eleusine EPSPS (WO 2001/66704). It can also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described, for example, in WO 2002/036782, WO 2003/092360, WO 2005/012515 and WO 2007/024782. Glyphosate-tolerant plants can also be obtained by selecting plants containing naturally occurring mutations of the above-mentioned genes as described, for example, in WO 2001/024615 or WO 2003/013226.

Other herbicide-resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition.

One such efficient detoxifying enzyme is, for example, an enzyme encoding a phosphinothricin acetyluansferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvatedioxy genase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally occurring resistant HPPD enzyme, or a gene encoding a mutated HPPD enzyme according to WO 1996/038567, WO 1999/024585 and WO 1999/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 1999/034008 and WO 2002/36787. Tolerance of plants to HPPD inhibitors can also be improved. by transforming plants with a gene encoding an enzyme prephenate dehydrogenase in addition to a gene encoding an HPPD-tolerant enzyme, as described in WO 2004/024928.

Further herbicide-resistant plants are plants that have been made tolerant to acetolactate synthase (ALS) inhibitors. Known ALS-inhibitors include, for example, sulphonylurea, imidazolinone, triazolopyrimidines, pyirimidinyloxy(thio) benzoates, and/or sulphonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed. Science (2002), 50, 700-712, but also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732, U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants are also described in for example WO 2007/024782.

Other plants tolerant to imidazolinone and/or sulphonylurea can be obtained by induced mutagenesis, selection in cell cultures in the presence of the herbicide or by mutation breeding as described for example for soya beans in U.S. Pat. No. 5,084,082, for rice in WO 1997/41218, for sugar beet in U.S. Pat. No. 5,773,702 and WO 1999/057965, for lettuce in U.S. Pat. No. 5,198,599 or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

The term "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, e.g. proteins of the Cry protein classes Cry1Ab, Cry1Ac, Cry1F, Cry2Ab, Cry3Ac or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol, (2001), 19, 668-72; Schnepf et al., Applied Eavironin. Microb. (2006), 71, 1765-1774); or
3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR604; or
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, e.g. proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT102.

Of course, insect-resistant transgenic plants, as used herein, also include any plant comprising a combination of genes encoding the proteins of any one of the abovementioned classes 1 to 8. In one embodiment, an insect-resistant plant contains more than one transgene encoding a protein of any one of the abovementioned classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include:

a. plants which contain a transgene capable of reducing the expression and/or the activity of the poly(ADP-ribose) polymerase (PARP) gene in the plant cells or plants as described in WO 2000/004173 or EP 04077984.5 or EP 06009836.5;
b. plants which contain a stress tolerance-enhancing transgene capable of reducing the expression and/or the activity of the PARG encoding genes of the plants or plant cells as described, for example, in WO 2004/090140;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase as described, for example, in EP 04077624.7 or WO 2006/133827 or PCT/EP07/002433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) transgenic plants which synthesize a modified starch, which in its physicochemical characteristics, in particular the amylase content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications. Said transgenic plants synthesizing a modified starch are described, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 and WO 1997/20936.
2) transgenic plants which synthesize non-starch carbohydrate polymers or which synthesize non-starch carbohydrate polymers with altered properties in comparison to wild type plants without genetic modification. Examples are plants producing polyfructose, especially of the in and levan type, as described in EP 0663956, WO 1996/001904, WO 1996/021023, 1998/039460 and WO 1999/024593, plants producing alpha-1,4-glucans, as described in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.
3) transgenic plants which produce hyaluronan, as for example described in WO 2006/032538, 2007/039314, WO 2007/039315, WO 2007/039316, JP 2006/304779 and WO 2005/012529.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, containing an altered form of cellulose synthase genes as described in WO 1998/000549,
b) plants, such as cotton plants, continuing an altered form of rsw2 or rsw3 homologous nucleic acids as described in WO 2004/053219;
c) plants, such as cotton plants, with increased expression of sucrose phosphate synthase as described in WO 2001/017333;
d) plants, such as cotton plants, with increased expression of sucrose synthase as described in WO 02/45485;
e) plants, such as cotton plants, wherein the timing of the plasmodesmatal gating at the basis of the fibre cell is altered, for example through downregulation of fibre-selective β-1,3-glucanase as described in WO 2005/017157;
f) plants, such as cotton plants, having fibres with altered reactivity, e.g. through the expression of the N-acetylglucosaminetransferase gene including nodC and chitin synthase genes as described in WO 2006/136351.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, producing oil having a high oleic acid content, as described, for example, in U.S. Pat. No. 5,969,169, U.S. Pat. No. 5,840,946 or U.S. Pat. No. 6,323,392 or U.S. Pat. No. 6,063,947;
b) plants, such as oilseed rape plants, producing oil having a low linolenic acid content, as described in U.S. Pat. No. 6,270,828, U.S. Pat. No. 6,169,190 or U.S. Pat. No. 5,965,755.

c) plants, such as oilseed rape plants, producing oil having a low level of saturated fatty acids, as described, for example, in U.S. Pat. No. 5,434,283.

Particularly useful transgenic plants which may be treated according to the invention are plants which comprise one or more genes which encode one or more toxins are the transgenic plants which are sold under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the following trade names: Roundup Ready® (tolerance to glyphosate, for example maize, cotton, soya bean), Liberty Link® (tolerance to phosphinotricin, for example oilseed rape), IMI® (tolerance to imidazolinones) and SCS® (tolerance to sulphonylureas), for example maize. Herbicide-resistant plants (plants bred in a conventional manner for herbicide tolerance) which may be mentioned include the varieties sold under the Clearfield® name (for example maize).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

Formulations:

The inventive succinate dehydrogenase inhibitors, preferably fluopyram, may be present in their commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers or semiochemicals.

In addition, the described positive effect of the succinate dehydrogenase inhibitors, preferably of fluopyram, on the control of *Sclerotinia* ssp. can be promoted by an additional treatment with insecticidal, fungicidal or bactericidal active ingredients.

Preferred application times for azole compounds to enhance resistance to abiotic stress are soil, stem and/or leaf treatments at the approved application rates.

The inventive succinate dehydrogenase inhibitors, preferably fluopyram, may generally additionally be present in their commercially available formulations and in the use forms, prepared from these formulations, as mixtures with other active ingredients, such as insecticides, attractants, sterilants, acaricides, nematicides, fungicides, growth regulators or herbicides.

The example which follows serves to illustrate the invention, but without restricting it.

EXAMPLE 1

In Brazil, a plot test was conducted with the soya variety Monsoy 7908 RR, in order to test the efficacy of fluopyram against *Sclerotinia sclerotiorum* in spray application under conditions of agricultural practice.

The products to be tested were sprayed onto the plants in the form of spraying sequences.

The periods between the individual sprayings varied between 2-3 weeks.

Fluopyram was applied in a 500 SC formulation (formulation number SP 102000016460) with application rates of 150, 200 and 250 g a.i./ha. The spray volume was 300 l of water per hectare.

30 days after the third spraying, the control success was evaluated visually in the plots. The rating was determined by counting the number of affected plants in parts of the plot. The efficacy was then calculated by the Abbott formula.

The numbers affected can be found in Table I below,

TABLE 1

Tab. 1 Efficiacy of fluopyram against *Sclerotinia sclerotiorum* in soya

| Treatment variant | Active ingredient dose (g a.i./ha) | Number of plants affected 30 days after the third spraying | Efficacy (% Abbott) |
|---|---|---|---|
| Untreated Control | | 17 | |
| Fluopyram | 150 | 2.7 | 84 |
| Fluopyram | 200 | 1.7 | 90 |
| Fluopyram | 250 | 0.3 | 98 |

The invention claimed is:

1. A method for controlling *Sclerotinia* spp. in oilseed rape or broad bean plants or plant parts thereof, said method comprises foliar treatment of said oilseed rape or broad bean plants or plant parts thereof in need of said controlling with between 0.1 to 1 kg fluopyram/ha, wherein fluopyram is the sole fungicide used in the method, to thereby control the *Sclerotinia* spp.

2. The method of claim 1, wherein the method consists essentially of treating said oilseed rape or broad bean plants or plant parts thereof with between 0.1 to 1 kg a.i./ha fluopyram.

3. The method of claim 1, wherein the *Sclerotinia* species is *Sclerotinia sclerotiorum.*

4. The method of claim 1, wherein the oilseed rape or broad bean plants are transgenic oilseed rape or broad bean plants or parts thereof.

5. The method of claim 1, wherein the method comprises treating oilseed rape plants or parts thereof.

6. The method of claim 1, wherein the method comprises treating broad bean plants or parts thereof.

7. The method of claim 1, comprising treatment of 150 to 250 g fluopyram/ha.

* * * * *